United States Patent [19]

Motoyuki et al.

[11] Patent Number: 5,744,670
[45] Date of Patent: Apr. 28, 1998

[54] PROCESS FOR PREPARING DIALKYLNAPHTHALENE

[75] Inventors: Masahiro Motoyuki; Koji Yamamoto, both of Kobe, Japan; John Paul McWilliams, Paulsboro; Robert Glenn Bundens, Pennington, both of N.J.

[73] Assignees: Kobe Steel, Ltd., Kobe, Japan; Mobil Oil Corporation, Fairfax, Va.

[21] Appl. No.: 661,114

[22] Filed: Jun. 10, 1996

[51] Int. Cl.[6] .................... C07C 2/00; C07C 2/66; C07C 5/22

[52] U.S. Cl. .................... 585/320; 585/312; 585/313; 585/314; 585/315; 585/323; 585/448; 585/450; 585/467; 585/471; 585/475; 585/478; 585/479; 585/481

[58] Field of Search ....................... 585/312, 313, 585/314, 315, 320, 323, 448, 450, 467, 471, 475, 478, 479, 481

[56] References Cited

U.S. PATENT DOCUMENTS

| | | |
|---|---|---|
| 4,795,847 | 1/1989 | Weitkamp et al. |
| 4,954,326 | 9/1990 | Odonera et al. ............ 423/328 |
| 5,001,295 | 3/1991 | Angevine et al. ............ 585/467 |

FOREIGN PATENT DOCUMENTS

| | | |
|---|---|---|
| 4 1142 | 1/1992 | Japan. |
| 4-1142 | 6/1992 | Japan. |

OTHER PUBLICATIONS

Chemical Abstracts, vol. 103, No. 5, 5 Aug. 1985, Columbus, Ohio, US; Abstract No. 37220t, p. 486; XP002037480 & JP 60 045 536A (Teijin Petrochemical Industries) 12 Mar. 1985.

Chemical Abstracts, vol. 82, No. 25, 23 Jun. 1975, Columbus, Ohio, Abstract No. 170491w, p. 498; XP002037481 & JP 49 134 661 A (Kurhea Chemical Industry Co) 25 Dec. 1974.

Primary Examiner—Glenn Caldarola
Assistant Examiner—Thuan D. Dang
Attorney, Agent, or Firm—Oblon, Spivak, McClelland, Maier & Neustadt, P.C.

[57] ABSTRACT

A process for producing alkylnaphthalene from a feedstock comprising isomers of dialkylnaphthalene and naphthalene by contacting the feedstock with a catalyst composition, in which the process comprising transalkylation between isomers of dialkylnaphthalene and naphthalene to produce monoalkylnaphthalene, and isomerization of dialkylnaphthalene, wherein the catalyst composition comprising a synthetic zeolite characterized by an X-ray diffraction pattern including interplanar d-spacing as set forth in Table A of the specification.

13 Claims, 1 Drawing Sheet

PROCESS FOR PREPARING DIALKYLNAPHTHALENE

FIELD OF THE INVENTION

This invention relates to a process for preparing alkylnaphthalene, and particularly to a method for preparing 2,6-dimethylnaphthalene(DMN) from naphthalene with an alkylating agent by using catalysts in both transalkylation and isomerization of DMN, as well as in alkylation of monomethylnaphthalene(MMN). This process is hereinafter described specifically by the preparation of 2,6-DMN, however, this process can be extentable to any dialkylnaphthalene.

BACKGROUND OF THE INVENTION

The compound 2,6-DMN is used as a precursor of 2,6-naphthalenedicarboxylic acid in the manufacture of polyester resins, because 2,6-DMN is easily oxidised to 2,6-naphthalenedicarboxylic acid compared with other precursors such as 2,6-diisopropylnaphthalene or 2-methyl-6-isobutyrylnaphthalenes.

There are a lot of proposal concerning the process for preparing the 2,6-DMN.

U.S. Pat. No. 4,795,847 (Weitkamp et al.) describes a process for the preparation of 2,6-dialkylnaphthalene by alkylating naphthalene or 2-alkylnaphthalene with an alkylating agent in the presence of a zeolite (specifically ZSM-5) as a catalyst.

U.S. Pat. No. 5,001,295 (Angevine et al.) describes process for preparing DMN by using 2-MN and naphthalene as a feedstock and a synthetic zeolite (MCM-22) as a catalyst, and it shows MCM-22 is more effective than ZSM-5 in alkylation of 2-MN and naphthalene.

However these conventional arts provide only unit operation for alkylation of 2-MN, which is an expensive feedstock and is not available in a large amount commercially. In addition, there is no description concerning how to use the DMN mixture(2,6-poor-DMN) after separation of 2,6-DMN, and the productivity of 2,6-DMN is not sufficient for mass production.

To increase the productivity of 2,6-DMN, it is preferrable to utilize and isomerize 2,6-poor-DMN to enrich 2,6-DMN in DMN isomers.

In order to utilize the 2,6-poor-DMN isomers effectively, the Japanese Patent Laid-Open No. 4-1142 shows a process to recycle the 2,6-poor-DMN isomers for isomerization, and combines transalkylation between of the 2,6-poor-DMN isomers with naphthalene to produce MMN. Produced MMN is alkylated with alkylating agent to produce DMN.

This process consists of 5 steps (1)~(5);

(1) 1st step (transalkylation and isomerization based on a modified ZSM-5 as a catalyst)
DMN+NL → MMN
DMN filtrate → 2,6-rich-DMN isomers (2) 2nd step (separation of the product of the 1st step into naphthalene, MMN and DMN by distillation)

(3) 3rd step (methylation of MMN using methylating agent to produce DMN)
MMN+methyl unit → DMN (4) 4th step (separation of the product of the 3rd step into MMN and DMN by distillation (5) 5th step (separation of 2,6-DMN from the DMN mixture of the second step and the 4th step by cooling crystallization)

According to the process, 2,6-poor-DMN isomers can be enrich 2,6-DMN at least to some extent. However yield of 2,6-DMN is still low.

The reasons of low yield of 2,6-DMN in the conventional process is considered to be based on the following two difficulties.

* difficulty of the effective isomerization

Ten isomers of DMN can be categorised into the following four groups (i)~(iv).

1,4-DMN ↔ 1,3-DMN ↔ 2,3-DMN    (i)

1,5-DMN ↔ 1,6-DMN ↔ 2,6-DMN    (ii)

1,8-DMN ↔ 1,7-DMN ↔ 2,7-DMN    (iii)

1,2-DMN    (iv)

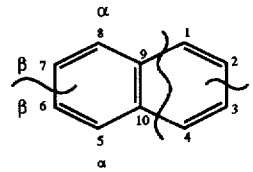

Isomerization within each groups is easily proceeded, however the isomerization beyond groups is very difficult to be carried out. It is due to the polarity of the naphthalene molecule which allows the methyl-transition between α-position and β-position (e.g. 1,5-DMN↔1,6-DMN), however transition between β-position and β-position (e.g. 2,6-DMN↔2,7-DMN) with the ring is not allowed easily. That is why isomerization of 2,6-poor-DMN isomers is not effective to enrich 2,6-DMN. In the above-mentioned Japanese Patent Laid-Open No. 4-1142, low catalyst performance in the transalkylation and the alkylation causes the low separation yield of 2,6-DMN from DMN isomers.

Therefore, it is very important to use a catalyst which has high selectivity of 2,6-DMN in isomerization.

*difficulty in separation of 2,6-DMN from DMN isomers

Furthermore it is very difficult to separate 2,6-DMN from other isomers by conventional separation methods such as distillation or cooling crystallization owing to the presense of 2,7-DMN.

In the distillation, 2,6-DMN and 2,7-DMN can not be separated each other because the difference of boiling point between 2,6-DMN and 2,7-DMN is only 0.3° C.

As for the cooling crystallization, since 2,6-DMN and 2,7-DMN forms an eutectic crystal at the weight ratio of 0.7(=2,6-DMN/2,7-DMN) the only low yield of 2,6-DMN is achieved. For example, according to the above-mentioned Japanese Patent Laid-Open No. 4-1142, the ratio of 2,6-DMN/2,7-DMN is 1.0. That is why the yield of 2,6-DMN is not high.

Consequently it is very important to increase the ratio of 2,6-DMN/2,7-DMN for the higher yeild of 2,6-DMN.

SUMMARY OF THE INVENTION

The present invention has been made in view of the foregoing situation and it intends to provide a process for preparing useful alkylnahthalene such as 2,6-DMN at a high yield.

Provided herein is a process for producing alkylnaphthalene from a feedstock comprising isomers of dialkylnaphthalene and naphthalene by contacting said feedstock with a catalyst composition, said process consisting essentially of transalkylation between isomers of dialkylnaphthalene and naphthalene to produce monoalkylnaphthalene, and isomerization of dialkylnaphthalene, wherein said catalyst composition comprising a synthetic zeolite characterized by an X-ray diffraction pattern including interplanar d-spacing as set forth in Table A.

TABLE A

| interplanar d-spacing (Å) | relative intensity $I/I_o \times 100$ |
|---|---|
| 12.36 ± 0.4 | M–VS |
| 11.03 ± 0.2 | M–S |
| 8.83 ± 0.14 | M–VS |
| 6.18 ± 0.12 | M–VS |
| 6.00 ± 0.10 | W–M |
| 4.06 ± 0.07 | W–S |
| 3.91 ± 0.07 | M–VS |
| 3.42 ± 0.06 | VS |

*The relative intensities are given in terms of the symbols; W = weak, M = medium, S = strong, VS = very strong.

DESCRIPTION OF THE PREFERRED EMBODIMENTS

Figure 1:
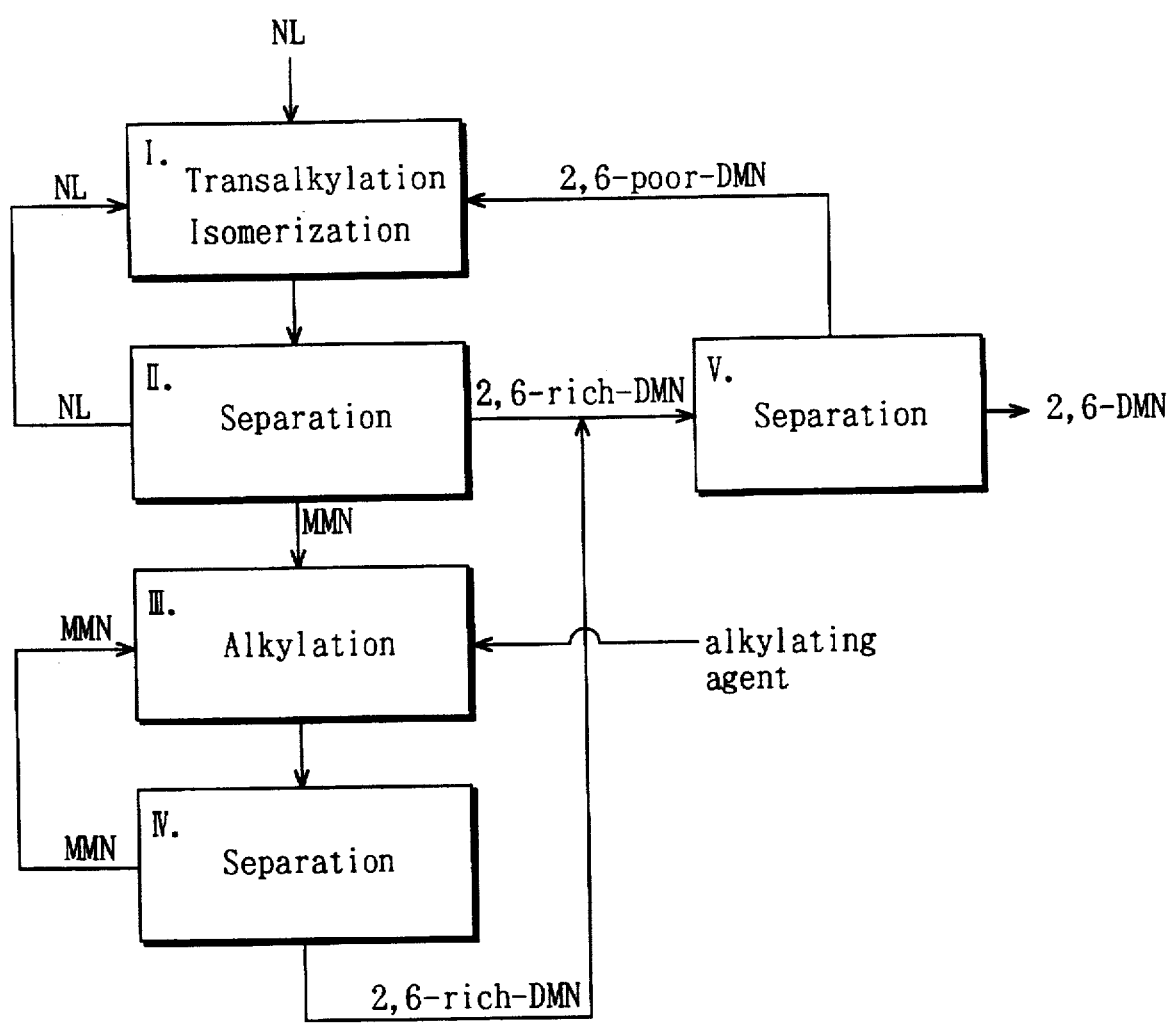
FIG. 1 is a schematic diagram to show preferable process of the present invention.

The present inventors have made earnest studies to higher the yield of 2,6-DMN, as a result, have accomplished the present invention based on the finding the the ratio of 2,6-DMN/2,7-DMN can be increased more than 1.2 by employing a particular catalyst in the transalylation and isomerization of 2,6-poor-DMN, as well as alkylation of MMN.

The particular catalyst is a zeolite which comprises a synthetic porous crystalline material characterized by an X-ray diffraction pattern including interplanar d-spacing can be set forth in the Table A.

The zeolite is known as MCM-22 and the entire contents of application Ser. No. 5,001,295 are incorporated herein by reference.

Transalkylation and isomerization conditions include a temperature of between about 0° to 500° C., and preferably between 240° and 450° C., and pressure of between 0 to 250 atmospheres and preferably 1 to 25 atmospheres. The mole ratio of naphthalene to DMN can be from about 1:1 to 1:10 and preferably can be from 1:1 to 1:5. The reaction is suitably accomplished utilizing a feed space velocity of between about 0.1 to 10.0 hr$^{-1}$.

In the transalkylation and isomerization of the present invention, 2,6-poor-DMN which contains less than 11 weight % of 2,6-DMN in the isomers is preferred as isomers of DMN in the feedsock, more preferably content of 2,6-DMN is less than 9%.

As mentioned above, a high raio of 2,6-DMN / 2,7-DMN is required to obtain high yeild of 2,6-DMN. According to the present invention, the ratio of 2,6-DMN / 2,7-DMN can be more than 1.2.

Further, the performance of catalyst in isomerization can be evaluated by a molar ratio of 2,6-DMN content in total DMN after isomerization against 2,6-DMN content in total DMN before isomerization. According to the present invention, this ratio can be more than 1.5.

By the way, the ratio between 2-MN and 1-MN is desired to be as high as possible because higher 2-MN / 1-MN ratio gives higher 2,6-DMN yield at alkylation. Theoritically the ratio is said to be around 2.2, however, it is difficult to achieve such a high ratio in the conventional process. According to the present invention, the ratio can he more than 2.0 in the transalkylation and isomerization by using MCM-22.

The present invention also provides a process for producing DMN from a feedstock comprising MMN and an alkylating agent with the catalyst MCM-22, and MMN of the feedstock is the separated MMN of the product by the transalkylation and isomerization. In this alkylation, the molar ratio of 2,6-dialkylnaphthalene / 2,7-dialkylnaphthalene of the alkylated product can be more than 1.1.

Furthermore, the present invention provides a process for producing 2,6-DMN from a feedstock comprising isomers of DMN and naphthalene by contacting the feedstock with the catalyst MCM-22, comprising step I [step for transalkylation between isomers of DMN and naphthalene to produce monomethylnaphthalene (MMN), and isomerization of DMN], step II [step for separation of the product in said step I into naphthalene, MMN and DMN], step III [step for methylation of MMN fraction from step II using methylating agent to produce DMN], step IV [step for separation of the product in said step III into MMN and DMN], step V [step for separation of 2,6-DMN from mixture of DMN fraction in said step II and said step IV].

In this process, as illustrated in FIG. 1, naphthalene fraction in step II recycles to step I, MMN fraction in step IV recycles to step III, DMN fraction after separated 2,6-DMN therefrom in step V recycles to step I.

As a method for separation of step II or step IV, distillation can be employed. To make this system simpler, step II and step IV can be combined as a single step by recycling the product of step III to step II.

As for separation of step V, any method for separation of isomers such as cooling crystallization or adsorption can be used. However, to obtain high yield of 2,6-DMN, High Pressure Crystallization is preferable.

Preferred alkylating agents include alcohols, olefins, aldehydes, halides, and ethers, such as methanol, dimethylether, polyalkylbenzene. Especially preferred is methanol.

The alkylation can be carried out in any of the known reactors usually employed for alkylation. For example, a tubular reactor with a downflow of reactants over a fixed bed of catalyst can be employed.

The present invention will now be explained refering to examles.

EXAMPLE 1

(Transalkylation and Isomerization)

30 grams of MCM-22 (¼"D×⅜"L, cylindrical pellet) are charged in a tubular reactor (volume: 122 cc). The reactor was heated from room temperature to 400° C. at the rate of 100° C./hr over introducing nitrogen gas into the reactor at atmospheric pressure.

As a feedstock for transalkylation and isomerization, isomers of DMN and naphtalene were used mixing DMN and naphtalene by 1:1 at molar ratio. Weight % of isomers of DMN is shown in Table 1.

TABLE 1

| (feedstock) | |
|---|---|
| component | weight % |
| dimethylnaphthalene | 99.70 |
| 2,6-DMN | 6.21 |
| 2,7-DMN | 8.63 |
| other isomers | 84.86 |
| monomethylnaphthalene | 0.30 |
| 2-MN | 0.17 |
| 1-MN | 0.13 |

The feedstock was introduced into the reactor at the rate of 30 g/hr for 8 hours, and obtained product was analyzed by gas chromatography. The result of the product is shown in Table 2 with the component of the reactant.

TABLE 2

| (transalkylation and isomerization) | | |
|---|---|---|
| component (wt %) | before reaction | after reaction |
| *dimethylnaphthalene | 53.19 | 39.41 |
| 2,6-DMN | 3.30 | 6.65 |
| 2,7-DMN | 4.59 | 4.59 |
| other isomers | 45.30 | 28.17 |
| *monomethylnaphthalene | 0.10 | 17.59 |
| 2-MN | 0.01 | 12.16 |
| 1-MN | 0.09 | 5.43 |
| *naphthalene | 46.71 | 38.15 |
| *other component | 0 | 4.85 |
| evaluation | before reaction | after reaction |
| 2,6-DMN/total DMN (%) | 6.2 ①  | 16.9 ② |
| 2,6-DMN/2,7-DMN | 0.72 | 1.45 |
| content of 2,6-DMN (after/before): @1 | — | 2.73 |
| NL conversion (%) | — | 18.3 |
| DMN conversion (%) | — | 25.9 |
| produced MMN/(converted DMN × 2): @2 | — | 0.70 |
| 2-MN/1-MN | — | 2.23 |

(note)
@1 in the table means a ratio of ②/① in 2,6-DMN/total DMN
@2 is caluculated on molar basis.

As can be seen from Table 2, the ratio of 2,6-DMN / 2,7-DMN is over 1.2 and the ratio of 2-MN / 1-MN is over 2.0.

EXAMPLE 2

(Transalkylation and Isomerization)

The same experiment with Example 1 except the molar ratio between DMN and naphtalene is 5:1 was carried out. The result of the product is shown in Table 3 with the component of the reactant.

TABLE 3

| (transalkylation and isomerization) | | |
|---|---|---|
| component (wt %) | before reaction | after reaction |
| *dimethylnaphthalene | 84.37 | 65.91 |
| *2,6-DMN | 5.22 | 11.39 |
| *2,7-DMN | 7.28 | 7.42 |
| other isomers | 71.87 | 47.10 |
| *monomethylnaphthalene | 0.17 | 13.81 |
| 2-MN | 0.02 | 9.54 |
| 1-MN | 0.15 | 4.27 |
| *naphthalene | 15.46 | 12.65 |

TABLE 3-continued

| (transalkylation and isomerization) | | |
|---|---|---|
| component (wt %) | before reaction | after reaction |
| *other component | 0 | 7.63 |
| evaluation | before reaction | after reaction |
| 2,6-DMN/total DMN (%) | 6.2 ① | 17.3 ② |
| 2,6-DMN/2,7-DMN | 0.72 | 1.53 |
| content of 2,6-DMN (after/before): @1 | — | 2.79 |
| NL conversion (%) | — | 18.2 |
| DMN conversion (%) | — | 21.9 |
| produced MMN/(converted DMN × 2): @2 | — | 0.41 |
| MMN 2-MN/1-MN | — | 2.23 |

(note)
@1 in the table means a ratio of 2/1 in 2,6-DMN/total DMN.
@2 is caluculated on molar basis.

As can be seen from Table 3, the ratio of 2,6-DMN / 2,7-DMN is over 1.2 and the ratio of 2-MN / 1-MN is over 2.0.

EXAMPLE 3

(Alkylation)

153 grams of MCM-22 were charged in the tubular reactor(volume:370 cc). As a feedstock for alkylation, 1-MN (purity 95.5%) and 2-MN (purity 96.6%) were used, and mixed at the molar ratio of 2.2 of 2-MN/1-MN. Feedstock was supplied in the reactor (350° C.) at the rate of 76.7 g/hr for 4 hours. Thereafter, methanol was started to be supplied in the reactor at the rate of 17.3 g/hr and the reaction proceeded for 20 hours. The obtained product was analyzed by gas chromatography, and the result is summarized in Table 4.

TABLE 4

| (alkylation) | | |
|---|---|---|
| component (wt %) | before reaction | after reaction |
| *dimethylnaphthalene | 0 | 35.45 |
| 2,6-DMN | 0 | 5.12 |
| 2,7-DMN | 0 | 4.44 |
| other isomers | 0 | 25.89 |
| *monomethylnaphthalene | 98.66 | 41.16 |
| 2-MN | 67.61 | 28.84 |
| 1-MN | 31.05 | 12.32 |
| *naphthalene | 0 | 0.19 |
| *other component | 1.53 | 23.20 |
| evaluation | before reaction | after reaction |
| 2-MN/1-MN | 2.2 | 2.3 |
| MN conversion (%) | — | 58.28 |
| 2,6-DMN/total DMN (%) | — | 14.45 |
| 2,6-DMN/2,7-DMN | — | 1.16 |

As can be seen from Table 4, the ratio of 2,6-DMN / 2,7-DMN is over 1.1 and the ratio of 2-MN / 1-MN is over 2.0.

EXAMPLE 4

(Alkylation)

153 grams of MCM-22 were charged in the tubular reactor(volume:370 cc). The same feedstock as in Example 3 was used. Feedstock was supplied in the reactor(400° C.) at the rate of 153.4 g/hr for 4 hours. Thereafter, methanol was started to be supplied in the reactor at the rate of 17.3 g/hr and the reaction proceeded for 20 hours. The obtained product was analyzed by gas chromatography, and the result is summarized in Table 5.

TABLE 5

| | (alkylation) | |
|---|---|---|
| component (wt %) | before reaction | after reaction |
| *dimethylnaphthalene | 0 | 5.05 |
| 2,6-DMN | 0 | 0.52 |
| 2,7-DMN | 0 | 0.37 |
| other isomers | 0 | 4.16 |
| *monomethynaphthalene | 98.66 | 89.01 |
| 2-MN | 67.61 | 59.84 |
| 1-MN | 31.05 | 29.17 |
| *naphthalene | 0 | 0 |
| *other component | 1.53 | 6.93 |
| evaluation | before reaction | after reaction |
| 2-MN/1-MN | 2.2 | 2.1 |
| MN conversion (%) | — | 9.78 |
| 2,6-DMN/total DMN (%) | — | 10.37 |
| 2,6-DMN/2,7-DMN | — | 1.42 |

As can be seen from Table 5, the ratio of 2,6-DMN / 2,7-DMN is over 1.1 and the ratio of 2-MN / 1-MN is over 2.0.

EXAMPLE 5

(Separation)

(1) high pressure crystallization 2,636 grams of DMN isomers were supplied into the high pressure crystallizer (KOBELCO 3L type), and separated 396 grams of 2,6-DMN crystals (purity 92%) at the condition of 2000 kgf/cm² and 45° C.

(2) cooling crystallization

Using vessel for crystallization (3 litter), 1,980 g of DMN isomers is cooled quickly from 50° C. to 40° C. over stirring slowly. Then, 0.5 grams of seed crystal was charged and kept the temperature at 40° C. for an hour. Thereafter, the feedstock was cooled to 10° C. at 2° C./min. 29.7 grams of 2,6-DMN crystals (purity 80%) was separated by filtration under pressure. The results of separation by both of high pressure crystallization and cooling crystallization are summarized in Table 6.

TABLE 6

| | (separation) | | |
|---|---|---|---|
| component (grams) | before crystallization | crystal | filtrate |
| HIGH PRESSURE CRYSTALLIZATION | | | |
| 2,6-DMN | 528 | 364 | 164 |
| 2,7-DMN | 405 | 32 | 373 |
| other DMN | 1,703 | 0 | 1,703 |
| TOTAL | 12,636 | 396 | 2,240 |
| 2,6-DMN/2,7-DMN | 1.3 | | 0.4 |
| 2,6-DMN/total DMN | 20.0 | | 7.3 |
| purity of crystal | — | 92% | — |
| recovery of 2,6-DMN | — | 69% | — |
| yield of 2,6-DMN | — | 13.8% | — |
| COOLING CRYSTALLIZATION | | | |
| 2,6-DMN | 396 | 237.6 | 158.4 |
| 2,7-DMN | 305 | 59.4 | 245.6 |
| other DMN | 1,286 | | 1,286 |
| TOTAL | 1,987 | 297 | 1,690 |
| 2,6-DMN/2,7-DMN | 1.3 | | 0.6 |

TABLE 6-continued

| | (separation) | | |
|---|---|---|---|
| component (grams) | before crystallization | crystal | filtrate |
| 2,6-DMN/total DMN | 19.9 | | 9.4 |
| purity of crystal | — | 80% | — |
| recovery of 2,6-DMN | — | 60% | — |
| yield of 2,6-DMN | — | 11.9% | — |

(note)
"recovery of 2,6-DMN" means the rate of 2,6-DMN content in crystal against of 2,6-DMN content in feedstock.
"yield of 2,6-DMN" means the rate of 2,6-DMN content in crystal against of total weight of feedstock.

As shown in Table 6, yield of 2,6-DMN by high pressure crystallization is much higher than by cooling crystallization. Further, 2,6-DMN / total-DMN of the filtrate by high pressure crystallization is less than 8%. Therefore, the filtrate is more effective as a feedstock for trasalkylation and isomerization of 2,6-poor-DMN. Furthermore, when the purity of crystal was tried to increase in cooling crystallization, the yield of 2,6-DMN was lowered drastically.

What is claimed is:

1. A process comprising:

contacting a feedstock comprising isomers of dialkylnaphthalene and naphthalene with a catalyst composition resulting in transalkylation between isomers of dialkylnaphthalene and said naphthalene to produce monoalkylnaphthalene; and isomerisation of isomers of dialkylnaphthalene to produce a dialkylnaphthalene isomerizate, wherein said catalyst composition comprises a synthetic zeolite characterized by an X-ray diffraction pattern including interplanar d-spacing 12.36±0.4
    11.03±0.2
    8.83±0.14
    6.18±0.12
    6.00±0.10
    4.06±0.07
    3.91±0.07
    3.42±0.06 Å wherein said process produces an increase in the amount of 2,6-dialkylnaphthalene.

2. The process of claim 1, wherein said feedstock comprises less than 11 weight % of 2,6-dialkylnaphthalene in said isomers.

3. The process of claim 1, wherein monoalkylnaphthalene is produced at a molar ratio of 2-monoalkylnaphthalene/1-monoalkylnaphthalene of more than 2.0.

4. The process of claim 1, wherein a product molar ratio of 2,6-dialkylnaphthalene/2,7-dialkylnaphthalene is more than 1.2.

5. The process of claim 1, wherein a molar ratio of 2,6-dialkylnaphthalene after isomerization / 2,6-dialkylnaphthalene before isomerization is more than 1.5.

6. The process of claim 1, further comprising separating said monoalkylnaphthalene.

7. The process of claim 6, further comprising contacting said monoalkylnaphthalene with an alkylating agent and an alkylation catalyst composition to produce an alkylate containing 2,6-dialkylnaphthalene.

wherein said alkylation catalyst composition comprises a synthetic zeolite characterized by an X-ray diffraction pattern including interplanar d-spacing 12.36±0.4
11.03±0.2
8.83±0.14
6.18±0.12
6.00±0.10
4.06±0.07
3.91±0.07
3.42±0.06 Å

8. The process of claim 7, wherein said alkylate has a ratio of 2,6-dialkylnaphthalene/2,7-dialkylnaphthalene of more than 1.1.

9. A process for producing 2,6-dialkylnaphthalene from a feedstock comprising isomers of dialkylnaphthalene and naphthalene comprising:

I) transalkylating isomers of dialkylnaphthalene and said naphthalene to produce monoalkylnaphthalene; and
isomerizing isomers of dialkylnaphthalene to produce a dialkylnaphthalene isomerizate;

II) separating the product of step I) into fractions of naphthalene, monoalkylnaphthalene and dialkylnaphthalene;

III) alkylating said fraction of monoalkylnaphthalene of step II) with an alkylating agent to produce dialkylnaphthalene;

IV) separating the product of step III) into fractions of monoalkylnaphthalene and dialkylnaphthalene; and V) separating 2,6-dialkylnaphthalene from said fractions of dialkylnaphthalene of steps II) and IV), wherein steps I) and III) are each conducted in the presence of a catalyst composition comprising a synthetic zeolite characterized by an X-ray diffraction pattern including interplanar d-spacing 12.36±0.4
11.03±0.2
8.83±0.14
6.18±0.12
6.00±0.10
4.06±0.07
3.91±0.07
3.42±0.06 Å

10. The process of claim 9 wherein said fraction of naphthalene of step II) is recycled to step I);
said fraction of monoalkylnaphthalene of step IV) is recycled to step III); and
a fraction of dialkylnaphthalene produced after separation of 2,6-dialkylnaphthalene of step V) is recycled to step I).

11. The process of claim 9, wherein 2,6-dialkylnaphthalene is separated from said fractions of dialkylnaphthalene by high pressure crystallization.

12. The process of claim 9 wherein said dialkylnaphthalene is dimethylnaphthalene and said monoalkylnaphthalene is monomethylnaphthalene.

13. The process of claim 1, wherein said catalyst composition comprises a synthetic zeolite characterized by an X-ray diffraction pattern including interplanar d-spacing and relative intensity $I/I_0 \times 100$ 12.36±0.4 M-VS
11.03±0.2 M-S
8.83±0.14 M-VS
6.18±0.12 M-VS
6.00±0.10 W-M
4.06±0.07 W-S
3.91±0.07 M-VS
3.42±0.06 Å VS.

* * * * *